United States Patent
Agus et al.

(10) Patent No.: US 7,955,810 B2
(45) Date of Patent: Jun. 7, 2011

(54) POSITIVE SELECTION OF SERUM PROTEINS FOR PROTEOMIC ANALYSIS

(75) Inventors: David B. Agus, Beverly Hill, CA (US); William Daniel Hillis, Encino, CA (US)

(73) Assignees: Cedars-Sinai Medical Center, Los Angeles, CA (US); Applied Proteomics, Inc., Glendale, CA (US)

( * ) Notice: Subject to any disclaimer, the term of this patent is extended or adjusted under 35 U.S.C. 154(b) by 257 days.

(21) Appl. No.: 12/515,388

(22) PCT Filed: Nov. 30, 2007

(86) PCT No.: PCT/US2007/086153
§ 371 (c)(1),
(2), (4) Date: May 18, 2009

(87) PCT Pub. No.: WO2008/070570
PCT Pub. Date: Jun. 12, 2008

(65) Prior Publication Data
US 2010/0055697 A1    Mar. 4, 2010

Related U.S. Application Data

(60) Provisional application No. 60/868,266, filed on Dec. 1, 2006.

(51) Int. Cl.
*G01N 1/00*    (2006.01)
*G01N 33/53*    (2006.01)

(52) U.S. Cl. ............ 435/7.21; 435/2; 435/7.1; 436/501; 436/518; 436/522; 422/50

(58) Field of Classification Search .................. None
See application file for complete search history.

(56) References Cited

U.S. PATENT DOCUMENTS

| 5,804,384 A | 9/1998 | Muller et al. |
|---|---|---|
| 6,551,788 B1 | 4/2003 | Bell |
| 2003/0003599 A1 | 1/2003 | Wagner et al. |
| 2006/0134712 A1 | 6/2006 | Stromgren et al. |

FOREIGN PATENT DOCUMENTS

| EP | 1580559 A1 | 9/2005 |
|---|---|---|
| WO | 2005094467 A2 | 10/2005 |

OTHER PUBLICATIONS

Anderson, N.L., The roles of multiple proteomic platforms in a pipeline for new diagnostics, Molecular & Cellular Proteomics, 2007, 4.10, pp. 1441-1444.
Anderson, N. L. et al., Mass spectrometric quantitation of peptides and proteins using stable isotope standards and capture by anti-peptide antibodies (SISCAPA), Journal of Proteome Research, 2004, 3:235-244.
Faca, V. et al., Contribution of protein fractionation to depth of analysis of the serum and plasma proteomes, Journal of Proteome Research, 2007, pp. A-G.
Tang, H. et al., A novel four-dimensional strategy combining protein and peptide separation methods enables detection of low-abundance proteins in human plasma and serum proteomes, Proteomics, 2005, 5:3329-3342.
Zolotarjova, N. et al., Removal and depletion of high-abundance proteins from biological fluids, LCGC North America, Feb. 2007, 25:2, pp. 118-140.

*Primary Examiner* — Lisa Cook
(74) *Attorney, Agent, or Firm* — Seth D. Levy; Davis Wright Tremaine LLP (57) ABSTRACT

This invention relates to methods and kits for positive selection of species of interest based on peptide/protein sequence from a biological sample. The species of interest may be proteins and/or peptides of interest which may be placed through a mass spectrometer to obtain a blood peptide/protein signature. The blood peptide/protein signature may be used in proteomic analysis. The techniques include but are not limited to the use of collectors comprising nucleic acid molecules to extract a composition that has a lower concentration of a high abundance species of interest from a sample. This limits the level of influence that any collectors species may have on the results of a mass spectra.

36 Claims, 6 Drawing Sheets

POSITIVE SELECTION OF SERUM PROTEINS FOR PROTEOMIC ANALYSIS

This application is the National Phase of International Application PCT/US07/86153, filed Nov. 30, 2007, which designated the U.S. and that International Application was published under PCT Article 21(2) in English. This application also includes a claim of priority under 35 U.S.C. §119(e) to U.S. provisional patent application No. 60/868,266, filed Dec. 1, 2006.

FIELD OF THE INVENTION

The invention relates to the field of proteomics; more specifically, to techniques for selecting proteins and/or peptides of interest from a sample for proteomic analysis.

BACKGROUND OF THE INVENTION

Proteomics refers to the qualitative and quantitative scientific analyses of the expression, localizations, functions and interactions of the proteins and peptides expressed by the genetic material of an organism. Proteomics and the technology commonly used therein find equal application in veterinary research, with other organisms and even non-living matter that contain appreciable quantities of proteins and/or peptides (e.g., soil, air). In proteomic research, proteins and peptides found in the human body, in other living organisms, and in non-living systems are analyzed for a wide array of purposes. For instance, in applications where proteins/peptides are collected from human subjects, proteomic analysis can be of great value in gaining a better understanding of metabolic pathways, in predicting the clinical outcome of therapeutic interventions to disease, or in elucidating the function of various organic molecules, to name but a few. There is significant potential with this discipline to expose heretofore unknown pathways and biochemical interactions that may lead to important findings in terms of human health and medicine. Indeed, many important biomarkers have been identified by application of this technology.

As noted above, one area of proteomic research involves the analysis of human proteins and peptides. With respect to mammalian subjects, and humans in particular, proteins and peptides may be readily collected through any number of methodologies and from any number of sources. By way of example, proteins and peptides may be found in mammalian body fluids, sera such as blood (including whole blood as well as its plasma and serum), CSF (spinal fluid), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysates, tumor tissue, hair, skin, buccal scrapings, nails, bone marrow, cartilage, prions, bone powder, ear wax, etc. or even from external or archived sources such as tumor samples (i.e., fresh, frozen or paraffin-embedded). Samples, such as body fluids or sera, obtained during the course of clinical trials may be particularly advantageous for use in connection with proteomic research, although samples obtained directly from living subjects under alternate conditions or for other purposes may be readily used as well.

Moreover, analysis of blood chemistry is routinely used in medicine for both diagnostic and prescriptive purposes. Currently, to analyze blood chemistry, a practitioner must order a series of tests or "panels" in which the concentration of a specific species or family of species within the blood serum is measured. For example, an electrolyte panel measures the concentrations of sodium, potassium, chloride, calcium and phosphorous. Performing such tests, however, can be time consuming and expensive. Furthermore, each panel focuses on a single species or family of species of interest, and is therefore limited in scope. It is therefore generally necessary for a practitioner to have, prior to ordering a panel, a suspicion of what species merit further analysis. In this sense, the practitioner must know ahead of time what he is looking for. A single test that returned a definitive blood chemistry signature upon which a wide range of diagnoses could be made and treatments prescribed would be very useful.

One approach to obtaining such a signature involves the direct determination of the concentration of all (or substantially all) species within the blood through mass spectroscopy. Difficulties arise, however, due to the extremely wide range of concentrations of species within the blood serum. In fact, regardless of the collection technique or the source of the proteins and peptides studied in connection with proteomics research, or the test used to collect a sample from a patient in obtaining a "panel," one limitation of this type of analysis, in general, is the difficulty in discerning small variations in the levels of proteins and peptides of relatively low abundance in a sample. For instance, there are thousands of different proteins and peptides present in a sample of serum obtained from a human subject. Some of these proteins and peptides are present in relatively high abundance, while others are present in relatively low abundance. Certain proteins of high abundance, such as albumin, immunoglobulin and transferrin are typically present in quantities of about $1 \times 10^{11}$ greater than proteins and peptides of relatively low abundance. This massive difference in protein/peptide abundance as between high abundance and low abundance proteins/peptides can obfuscate the detection of small variations in proteins of low abundance. It is essentially a signal to noise ratio problem in the mass spectroscopy measurement, wherein the signatures of the lower concentration species are lost beneath the noise floor. The dynamic range of the analysis device (e.g., mass spectrometer) is at best 4-5, not close to the 11 orders of magnitude dynamic range of the serum proteome. In a typical mass spectrum based on a mammalian serum sample, there are number of proteins/peptides that are present in high abundance therein, as demonstrated by the series of large peaks in a mass spectra readout. The presence and quantity of the vast array of proteins/peptides of relatively low abundance are more difficult to discern.

This is especially problematic in conducting a comparative proteomic analysis of sera collected from multiple human subjects. The proteins and peptides of relatively high abundance in human sera are, generally speaking, the same for all human subjects (e.g., albumin, immunoglobulin and transferrin). It is frequently the presence and/or variation in quantity of proteins and peptides of relatively low abundance among different subjects that is most instructive in terms of gaining knowledge about human biology, medicine, disease and the like. Therefore, if the ability to discern the presence and/or variations in the quantity of proteins and peptides of low abundance is impeded, then the overall value of proteomic research in this field may ultimately be compromised.

There are a number of techniques commonly used in the art to "negatively select" the proteins and/or peptides of interest in a sample. These techniques may be used to help address the aforementioned problems. In negative selection techniques, unwanted molecules are removed from a sample, leaving behind only the proteins/peptides of interest. Examples of this type of selection include Enchant™ Life Science Kits for Albumin Depletion (available from Pall Corporation, New York, N.Y.), Agilent's Multiple Affinity Removal System via a Liquid Chromatography Column or as a Spin Cartridge (both available from Agilent Technologies, Palo Alto, Calif.), and high performance liquid chromatography.

However, negative selection techniques are oftentimes unsuccessful. Quantities of proteins and/or peptides of interest may be inadvertently removed from the sample along with the unwanted molecules when performing negative selection. Conversely, a significant volume of unwanted molecules frequently remains in the sample along with the proteins and/or peptides of interest. Either or both of these complications may lead to inaccurate or incomplete proteomic analyses of the resulting sample, and, in extreme situations, may render the samples entirely unusable.

There are positive selection methods based on glycosylation. For example, identification and quantification of peptides containing N-linked carbohydrates based on the conjugation of glycoproteins to a solid support medium using hydrazide chemistry, stable isotope labeling of the glycopeptides and specific release of formerly N-linked glycopeptides by peptide N-glycosidase F are available (Institute for Systems Biology; Seattle, Wash.). These methods reduce the dynamic range by several orders of magnitude but significant amounts of low abundance peptides are lost to analysis through this process. This technique is based on selection based on a post-translational modification, not on a quality of the actual peptide itself. There is therefore a need in the art for a technique to obtain a sample of proteins and/or peptides of interest for proteomic analysis that is substantially free from the aforementioned limitations of negative and crude positive selection procedures. There is a further need in the art for a procedure to ascertain a definitive blood chemistry signature for diagnostic and prognostic purposes; particularly if that procedure could alone serve as sufficient evidence for a wide range of medical diagnoses and prescriptions. Ideally, the procedure would return a blood chemistry signature that qualifies, to as great an extent as possible, the chemical composition of a patient's blood.

SUMMARY OF THE INVENTION

The present invention relates to methods and kits for selecting proteins and/or peptides of interest from a sample. The proteins/peptides so selected may be used in connection with proteomic analysis. Specifically, the present invention incorporates techniques for the "positive selection" of proteins and/or peptides of interest to prepare samples for proteomic analysis based on peptide/protein sequence. Any positive selection technique based on peptide/protein sequence may be implemented in accordance with various embodiments of the present invention.

Several embodiments of this selection technique are described herein, and are considered to be illustrative of the type of positive selection techniques based on peptide/protein sequence that are appropriate for use in connection with proteomic sample preparation in accordance with the present invention.

The present invention provides a method to extract a composition comprising a plurality of species of interest and a lower concentration of a high abundance species of interest from a sample, comprising: providing a plurality of collectors capable of binding specifically with a sufficient binding affinity to a plurality of species of interest in a sample comprising at least one high abundance species of interest, wherein the quantity of a collector specific for the at least one high abundance species of interest may be at least 50% less than the quantity of the at least one high abundance species of interest in the sample; placing the sample in contact with the plurality of collectors, whereby at least a portion of the plurality of collectors binds to the species of interest to generate bound species of interest, and at least 75% of the collector specific for the at least one high abundance species of interest binds to the at least one high abundance species of interest to generate bound high abundance species of interest; and separating the bound species of interest and the bound high abundance species of interest from the sample to generate an extracted composition, whereby the concentration of the at least one high abundance species of interest in the extracted composition may be lower than the concentration of the at least one high abundance species of interest in the sample, wherein the species of interest may be selected from the group consisting of a protein, protein fragment, peptide and combinations thereof, and the plurality of collectors may comprise a collector type selected from the group consisting of a nucleic acid molecule, amino acid, peptide, protein, aptamer, antibody, plasmid, phage, cofactor, metal ion and combinations thereof. In various embodiments of the method, the at least one high abundance species of interest may be selected from the group consisting of albumin, immunoglobulin, transferrin and combinations thereof. In other embodiments of the method, the quantity of the collector specific for the at least one high abundance species of interest may be at least 75% less than the quantity of the at least one high abundance species of interest in the sample. In another embodiment of the method, the quantity of the collector specific for the at least one high abundance species of interest may be at least 85% less than the quantity of the at least one high abundance species of interest in the sample. In another embodiment of the method, the quantity of the collector specific for the at least one high abundance species of interest may be at least 95% less than the quantity of the at least one high abundance species of interest in the sample. In various embodiments of the method, placing the sample in contact with the plurality of collectors may bind at least 85%, 90%, 95%, or 99% of the collector specific for the at least one high abundance species of interest to the at least one high abundance species of interest to generate the bound high abundance species of interest. In various embodiments of the method, separating the bound species of interest and the bound high abundance species of interest from the sample may comprise: separating collectors bound to the species of interest and collectors bound to the high abundance species of interest from the sample; and/or separating the bound species of interest and the bound high abundance species of interest from the collectors. In various embodiments of the method, the sample may be selected from the group consisting of body fluids, whole blood, plasma, serum, cerebral spinal fluid (CSF), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysate, tumor tissue, hair, skin, buccal scraping, nail, bone marrow, cartilage, prion, bone powder, ear wax, tumor samples and combinations thereof. In particular embodiments of the method, the sample may be whole blood, blood plasma or blood serum. In other particular embodiments of the method, the nucleic acid molecule may be a DNA aptamer or a RNA aptamer. In a particular embodiment of the method, the collector type may comprise genomic DNA cleaved into segments. In another particular embodiment of the method, the collector type may be an antibody capable of binding specifically to a particular protein, protein fragment, and/or peptide.

The present invention also provides for a method for producing set of collectors to extract a composition comprising a plurality of species of interest and a lower concentration of a high abundance species of interest from a sample, comprising: providing a set of random collectors; exposing a sample comprising a plurality of species of interest to the set of random collectors; removing at least one unbound collector; providing at least one additional random collector; and repeating the process until a desired collector set is obtained. In one embodiment of this method, the collectors may comprise a collector type that is a nucleic acid molecule. In particular embodiments, the nucleic acid molecule may be a DNA aptamer or a RNA aptamer. In other embodiments, the species of interest may be selected from the group consisting of a protein, protein fragment, peptide and combinations thereof.

The present invention also provides for a kit for extracting a composition comprising a plurality of species of interest and a lower concentration of a high abundance species of interest from a sample, comprising: a plurality of collectors capable of binding specifically with a sufficient binding affinity to a plurality of species of interest in a sample comprising at least one high abundance species of interest, wherein the quantity of a collector specific for the at least one high abundance species of interest is at least 50% less than the quantity of the at least one high abundance species of interest in the sample; and instructions for using the plurality of collectors to extract a composition comprising the plurality of species of interest and a lower concentration of the high abundance species of interest from the sample, wherein the species of interest may be selected from the group consisting of a protein, protein fragment, peptide and combinations thereof, and the plurality of collectors may comprise a collector type selected from the group consisting of a nucleic acid molecule, amino acid, peptide, protein, aptamer, antibody, plasmid, phage, cofactor, metal ion and combinations thereof. In various embodiments of the kit, the nucleic acid molecule may be a DNA aptamer or RNA aptamer. In a particular embodiment of the kit, the collector type may comprise a genomic DNA. In another particular embodiment of the kit, the collector type may be an antibody capable of binding specifically to a particular protein, protein fragment, or peptide.

The present invention also provides for a method of obtaining a blood chemistry signature, comprising: obtaining a sample from a subject, wherein the sample comprises at least one high abundance species of interest; providing a plurality of collectors capable of binding specifically with a sufficient binding affinity to a plurality of species of interest in the sample, wherein the quantity of a collector specific for the at least one high abundance species of interest is at least 50% less than the quantity of the at least one high abundance species of interest in the sample; placing the sample in contact with the plurality of collectors, whereby at least a portion of the plurality of collectors binds to the species of interest to generate bound species of interest, and at least 75% of the collector specific for the at least one high abundance species of interest binds to the at least one high abundance species of interest to generate bound high abundance species of interest; separating the bound species of interest and the bound high abundance species of interest from the sample to generate an extracted composition, whereby the concentration of the at least one high abundance species of interest in the extracted composition is lower than the concentration of the at least one high abundance species of interest in the sample; and performing a mass spectrometric analysis of the extracted composition, wherein the species of interest may be selected from the group consisting of a protein, protein fragment, peptide and combinations thereof, and the plurality of collectors comprise a collector type selected from the group consisting of a nucleic acid molecule, amino acid, peptide, protein, aptamer, antibody, plasmid, phage, cofactor, metal ion and combinations thereof. In various embodiments of the method, the at least one high abundance species of interest may be selected from the group consisting of albumin, immunoglobulin, transferrin and combinations thereof. In one embodiment, the quantity of the collector specific for the at least one high abundance species of interest may be at least 75% less than the quantity of the at least one high abundance species of interest in the sample. In another embodiment, the quantity of the collector specific for the at least one high abundance species of interest may be at least 85% less than the quantity of the at least one high abundance species of interest in the sample. In another embodiment, the quantity of the collector specific for the at least one high abundance species of interest may be at least 95% less than the quantity of the at least one high abundance species of interest in the sample. In various embodiments, placing the sample in contact with the plurality of collectors may bind at least 85%, 90%, 95%, or 99% of the collector specific for the at least one high abundance species of interest to the at least one high abundance species of interest to generate the bound high abundance species of interest. In additional embodiments, separating the bound species of interest and the bound high abundance species of interest from the sample may comprise: separating collectors bound to the species of interest and collectors bound to the high abundance species of interest from the sample; and/or separating the bound species of interest and the bound high abundance species of interest from the collectors. In various embodiments, the sample may be selected from the group consisting of body fluids, whole blood, plasma, serum, cerebral spinal fluid (CSF), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysate, tumor tissue, hair, skin, buccal scraping, nail, bone marrow, cartilage, prion, bone powder, ear wax, tumor samples and combinations thereof. In particular embodiments, the sample may be whole blood, blood plasma or blood serum. In various embodiments, the nucleic acid molecule may be a DNA aptamer or a RNA aptamer. In one embodiment, the collector type comprises genomic DNA cleaved into segments. In another embodiment, collector type is an antibody capable of binding specifically to a particular protein, protein fragment, and/or peptide.

The present invention also provides for a kit for obtaining a blood chemistry signature, comprising: a plurality of collectors capable of binding specifically with a sufficient binding affinity to a plurality of species of interest in a sample comprising at least one high abundance species of interest, wherein the quantity of a collector specific for the at least one high abundance species of interest is at least 50% less than the quantity of the at least one high abundance species of interest in the sample; instructions for using the plurality of collectors to extract a composition comprising a plurality of species of interest and a lower concentration of a high abundance species of interest from a sample; and instructions for analyzing the extracted composition, wherein the species of interest may be selected from the group consisting of a protein, protein fragment, peptide and combinations thereof, and the plurality of collectors may comprise a collector type selected from the group consisting of a nucleic acid molecule, amino acid, peptide, protein, antibody, plasmid, phage, cofactor, metal ion and combinations thereof. In various embodiments of the kit, the nucleic acid molecule may be a DNA aptamer or a RNA aptamer. In one embodiment of the kit, the collector type may comprise genomic DNA cleaved into segments. In another embodiment of the kit, the collector type may be an antibody capable of binding specifically to a particular protein, protein fragment, and/or peptide.

After the collector set has been exposed to the sample, the collectors of each collector type may be in one of three states: (1) completely empty (i.e., no species from within the sample bound to any of the collectors of that collector type), indicating that the species of interest is not present in the sample at detectable levels; (2) partially filled (i.e., species from within the sample bound to some but not all of the collectors of that collector type), indicating that the species is present at an intermediate concentration; or (3) completely filled (i.e., species from within the sample bound to all of the collectors of that collector type), indicating that the species is highly prevalent.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Antibody" or "antibodies" as used herein include but are not limited to polyclonal antibodies, monoclonal antibodies, antibody variants such as single chain (recombinant) Fv, humanized antibodies, chimeric antibodies, and immunologically active fragments of antibodies.

"Aptamer" as used herein refers to a nucleic acid molecule or a peptide molecule that bind to a specific target molecule, such as a species of interest. Aptamers include DNA aptamers, RNA aptamers and peptide aptamers.

"Binds specifically" as used herein refers to the act of a collector binding to its species of interest and is intended exclude low-level, non-specific binding that may occur between random nucleic acid molecules and/or proteins. "Binds specifically" as used herein is not intended and does not imply that the collector will not bind to any species of interest since collectors such as antibodies can cross-react with any protein that includes the relevant epitope.

"Collector" as used herein refers to any suitable organic molecule, inorganic molecule, submicroscopic agents (e.g., phage) or material with a sufficient binding affinity for species of interest. Examples of collectors include but are not limited to nucleic acid molecules (e.g., nucleotides, oligonucleotides, polynucleotides, DNA, RNA DNA aptamers, RNA aptamers), amino acids, peptides, proteins (native or recombinant), peptide aptamers, antibodies, plasmids, phages, cofactors, and metal ions.

"Genomic DNA" as used herein refers to the full complement of DNA contained in the genome of a cell or organism.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Species of interest" as used herein refers to any target analyte that is to be selected out of a sample. Examples include, but are not limited to, molecules, microorganisms, submicroscopic agents, proteins, protein fragments, peptides, cells, antibodies, DNA, RNA, and organelles.

"Sufficient binding affinity" as used herein refers to an amount of attraction and binding strength between a collector type and a species of interest that results in a binding of at least a portion of the species of interest to the collector type.

The present invention provides for a method for positive selection of species of interest from a sample.

In one embodiment, the positive selection is accomplished by a method to extract a composition comprising a plurality of species of interest and a lower concentration of a high abundance species of interest from a sample. The method may comprise providing a plurality of collectors capable of binding specifically with a sufficient binding affinity to a plurality of species of interest in a sample comprising at least one high abundance species of interest, wherein the quantity of a collector specific for the at least one high abundance species of interest may be at least 50%, 75%, 85%, or 95% less than the quantity of the at least one high abundance species of interest in the sample. As such, when all or almost all the collector specific for the high abundance species of interest are bound, only a limited quantity of the high abundance species of interest will be extracted out of the sample. Thus, a signal from the high abundance species of interest in the extracted sample will be clipped when the extracted sample is subjected to mass spectrometric analysis. Accordingly, presence and/or quantity of proteins, protein fragments, and/or peptides that are of relatively low abundance in a sample can be more easily discernable in a mass spectrum.

The method may further comprise placing the sample in contact with the plurality of collectors, whereby at least a portion of the plurality of collectors binds to the species of interest to generate bound species of interest, and at least 75%, 85% or 95% of the collector specific for the at least one high abundance species of interest binds to the at least one high abundance species of interest to generate bound high abundance species of interest. The method may also further comprise separating the bound species of interest and the bound high abundance species of interest from the sample to generate an extracted composition. The extracted composition will have the species of interest wherein the concentration of the at least one high abundance species of interest in the extracted composition is lower than the concentration of the at least one high abundance species of interest in the sample. Again, since not all of the high abundance species of interest can bind to the collector that is specific for the high abundance species of interest, a portion of the high abundance species of interest will be left behind in the sample when the composition is extracted from the sample by removing the bound species of interest (low abundance species and high abundance species).

In various embodiments, the species of interest may be, for example, a protein, protein fragment, and/or a peptide. Other species of interest may also be extracted from the sample. The plurality of collectors may comprise a collector type selected from the group consisting of a nucleic acid molecule, amino acid, peptide, protein, aptamer, antibody, plasmid, phage, cofactor, metal ion and combinations thereof.

In this method, the concentration of a high abundance species of interest, such as albumin, immunoglobulin, transferrin is reduced in the extracted composition.

The sample from which the composition is extracted may be selected from the group consisting of body fluids, whole blood, plasma, serum, cerebral spinal fluid (CSF), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysate, tumor tissue, hair, skin, buccal scraping, nail, bone marrow, cartilage, prion, bone powder, ear wax, tumor samples and combinations thereof.

The present invention also provides for a set of collectors constructed to selectively bind species of interest from within a sample that contains such species. In one embodiment, the collectors are adapted to bind proteins, protein fragments and/or peptides contained in blood serum. The collectors may be any suitable organic molecule, inorganic molecule, sub-microscopic agent or material with a sufficient binding affinity for species of interest. Examples of collectors include, but are not limited to nucleic acid molecules (e.g., nucleotides, oligonucleotides, polynucleotides, aptamers, and all of which may be DNA or RNA), amino acids, peptides, proteins (native or recombinant), peptide aptamers, antibodies, plasmids, phages, cofactors, and metal ions. The bound species, either alone or together with the collectors, may be analyzed, for example, in a mass spectrometer to yield a blood chemistry signature. It is also contemplated that in some embodiments, the collectors and the species of interest may be the same; for example, DNA collectors to select for DNA molecules, and RNA collectors to select for RNA molecules.

The aforementioned collector set may include collectors selected from a library of collector types. Some or all collector types may be repeated numerous times within the collector set.

Each collector type should have sufficient binding affinity to the species of interest. In one embodiment, the sufficient binding affinity is approximately equal to the dissociation constant "$K_d$" for the species of interest. In one embodiment, a collector type has a dissociation constant that is approximately equal to the average concentration of the species of interest. This is beneficial as it provides the best measure of variability across samples. That is, it will not be saturated to the same value across all samples. For example, the dissociation constant may be determined by the following formula:

$$K_d = \frac{SC}{B}$$

wherein S, C and B represents the concentrations of the species of interest, collector, and the bound complex (i.e., the species of interest bound to the collector), respectively.

In various embodiments of the present invention, a predetermined collector set is provided, wherein the composition of the collector set is known. That is, the collector set comprises known collectors specific for particular species of interest.

In other embodiments of the present invention, the specific composition of the collector set need not be known explicitly, so long as its use in connection with the invention is controlled and repeatable. This set of collectors can be used for extracting a composition comprising a plurality of species of interest and a lower concentration of a high abundance species of interest from a sample. The extracted sample may be used in proteomic research, which may be performed by mass spectrometric analysis of the extracted sample. A method of producing this set of collectors may comprise: providing a set of random collectors; exposing a sample comprising a plurality of species of interest to the set of random collectors; removing at least one unbound collector; providing at least one additional random collector; and repeating the process until a desired collector set is obtained.

For example, as shown in FIG. 2, a collector set is developed as follows: (A) Support media 211, collectors 221, 222, 223, 224, 225, 226 (e.g., DNA aptamers) and a sample with the species of interest 231, 232, 235, 237, 238, 239 (e.g., proteins) are provided. (B) An initial set of random collectors 221, 222, 223, 224, 225, 226 are affixed to support media 211 (e.g., glass beads) and a sample 230 containing the species of interest is placed in contact with the initial random set of collectors. (C) Some collectors (221, 222, 225) will bind to species of interest (231, 232, 235) and other collectors (223, 224, 226) will not bind to species of interest; similarly, some species of interest will remain unbound (231, 232, 237, 238, 239). This may be because the particular collector is not present or because the particular collector has been bound. (D) The unbound collectors (223, 224, 226) are replaced by additional random collectors 227, 228, 220, and the sample 230 is again placed in contact with the collectors. (E) Some of the new collectors (227, 228) will bind to species of interest and other new collector(s) (220) will not bind to species of interest, similarly, some species of interest will remain unbound (231, 232, 239). This again may be because the particular collector is not present or because the particular collector has been bound (e.g., collector 221 for species of interest 231, collector 222 for species of interest 232). The process is repeated until an entire collector set is established. This method of establishing a collector might not yield the actual identity of the collector set. However, this method is repeatable and a desired collector set may be established each time.

Aptamers (e.g., DNA, RNA and peptide) are particularly useful and may be used as collectors for positive selection of serum proteins. Aptamers are able to bind to various molecular targets, such as proteins, with high specificity. (See e.g., Bunka et al., *Aptamers come of age—at last*. NAT. REV. MICROBIOL. 2006 August; 4(8):588-596; O'Sullivan, *Aptasensors—the future of biosensing?* ANAL. BIOANAL. CHEM. 2002 January; 372(1):44-48.) Thus, each collector type in a collector set may be a different aptamer that specifically binds a protein or protein fragment. One of skill in the art will be able to engineer aptamers to target particular proteins without undue experimentation; for example, through repeated rounds of in vitro selection. Archemix and Aptares are examples of companies that synthesize and isolate aptamers.

The collector set may be configured in an apparatus in such a way that each collector is bound to a support medium. One of skill in the art will appreciate a variety of support media that can be used in various embodiments of the present invention. Examples of support media include, but are not limited to glass, agarose, cellulose, cross linking polymers, plastic, and silicone; these materials may exist in various forms, such as beads or chips. The collector set may then be contacted with the species-containing sample (e.g., blood serum) in a repeatable laboratory procedure. In embodiments of the present invention wherein beads are used, the beads may be placed in a column through which the species-containing sample flows. As the collector set contacts the sample, each collector type may selectively bind a particular species therein.

In another embodiment of the present invention, the collectors may be labeled for detection; for example, the collectors may be labeled with a fluorescent marker, fluorophore, chromophore, quantum dot, or isotope (e.g., isotopically modified) for detection. Labeled collectors may be placed in contact with the sample and each collector may selectively bind a particular species therein. The sample may be placed through a sorting device to separate the labeled collectors and the species of interest that are bound to the labeled collectors from the remainder of the sample. In one embodiment, flow cytometry may be used to sort the sample and separate labeled collectors and the species of interest that are bound to the labeled collectors from the remainder of the sample. The fraction that contains the labeled collectors and the species of interest that are bound to the labeled collectors may be processed to separate the species of interest from the collectors.

After the collector set has been exposed to the sample, the collectors of each collector specific to a species of interest will be in one of three states: (1) completely empty (i.e., no species from within the sample bound to any of the collectors of that collector type); (2) partially filled (i.e., species from within the sample bound to some but not all of the collectors of that collector type); or (3) completely filled (i.e., species from within the sample bound to all of the collectors of that collector type). In various embodiments, a collector that is almost completely filled (e.g., 95%, 96%, 97%, 98%, 99%) may be categorized as completely filled; for example, for purposes of indicating that it is a collector for a high abundance species of interest.

In one embodiment of the present invention, the bound species may then be separated from the collectors and subjected to a mass spectroscopy analysis to generate a blood chemistry signature. Alternatively, the collectors and bound species may together be subjected to a mass spectroscopic analysis.

Separation of bound species from the collectors may be accomplished by any appropriate method known in the art. Appropriate method for separation will depend on the type of collector and bound species. Examples of separation methods include, but are not limited to manipulating the pH, electric charge, hydrophobic, hydrophilic, temperature, and/or magnetic charge of a sample containing the bound species and the collectors. For example, in one embodiment, if the collector is also bound to a support medium in a column apparatus, a buffer that decreases the species' affinity to the collector may be used to elute the species of interest. In another embodiment, an increase in temperature may cause dissociation of the species of interest from the collectors.

A mass spectrometer is an instrument that measures the masses of individual molecules that have been converted into ions, i.e., molecules that have been electrically charged. A mass spectrometer measures the mass-to-charge ("m/z") ratio of the ions formed from the molecules. The sample, which may be a solid, liquid, or vapor, enters a vacuum chamber through an inlet. Depending on the type of inlet and ionization techniques used, the sample may already exist as ions in solution, or it may be ionized in conjunction with its volatilization or by other methods in the ion source. The gas phase ions are sorted in the mass analyzer according to their m/z ratios and then collected by a detector. In the detector the ion flux is converted to a proportional electrical current. A data system records the magnitude of these electrical signals as a function of m/z and converts this information into a mass spectrum. U.S. Pat. Nos. 6,504,150 and 6,960,760 are examples and provide further information on mass spectrometers and their use.

The library of collector types may contain at least one collector type for each species of interest within a sample. In this embodiment of the present invention, the aforementioned outcome (1), completely empty, indicates that the species of interest is not present in the sample at detectable levels; and outcome (3), completely filled, indicates that the species is highly prevalent and has saturated the dynamic range of the test. Outcome (2), partially filled, indicates that the species is present at an intermediate concentration.

In one embodiment of the present invention, the fraction of collectors of a particular collector type at which binding occurs is mapped to the concentration of the binding species in the sample. Typically, a correlation is made between the number of collectors of a given type which are available to bind a protein and the number of protein molecules bound to the collector type. By determining the number of bound collectors, a determination and/or estimate of the number and/or quantity of the specific protein present in the original sample may be made. However, this is not strictly necessary for a chemistry signature of the sample to be useful. Rather, it is only necessary that the process be repeatable and dispersive. That is, a range of species concentrations in the sample must produce a range of fractions of bound collectors, rather than collapsing onto a single fraction of bound collectors.

The ability of the collectors of a particular collector type to saturate (outcome (3)) is an important aspect of the invention, as it limits the level of influence that any one species, particularly a high abundance species, may have in the determined signature. Essentially, the mass spectroscopy signal is "clipped", greatly improving the signal to noise ratio problem described earlier. By limiting the influence (i.e., clipping its signal) of one or more species that would otherwise be abundant in a sample, the mass spectrometer may more effectively detect variations of low abundance species as their signals are not overshadowed by high abundance species. Examples of high abundance proteins include, but are not limited to albumin, immunoglobulin, transferrin, factor H, C9 complement, C8 complement, C5 complement, C6 complement, C7 complement, fibrinogen; examples of low abundance protein include but are not limited to cytokines, signaling molecules, intracellular proteins, interleukin-4, TNF alpha, interferon gamma, interleukin-1 Beta, interleukin-12, interleukin-5, interleukin-10, and interleukin-6 (N. Leigh Anderson and Norman G. Anderson, *The Human Plasma Proteome: History, Character, and Diagnostic Prospects*, MOLECULAR & CELLULAR PROTEOMICS 1:845-867, 2002.) It is not intended that this would be an exhaustive list of high abundance proteins and low abundance proteins. One of skill in the art will recognize additional high abundance proteins and additional low abundance proteins that are in a biological sample. This is especially the case for low abundance proteins as there are a vast variety of low abundance proteins. The proteins (high abundance and low abundance) may be selected out of the sample and the signal of the high abundance proteins and low abundance proteins may be clipped or enhanced, respectively.

To encourage widespread adoption and applicability of the procedure, the collector set may be both standardized and easily replicated. To this end, a particular embodiment is directed to creating a collector set using nucleic acid molecules (DNA, RNA, DNA aptamers and/or RNA aptamers). This choice of collector has the advantage of being very easily replicated through existing nucleic acid manipulation techniques.

Figure 3:
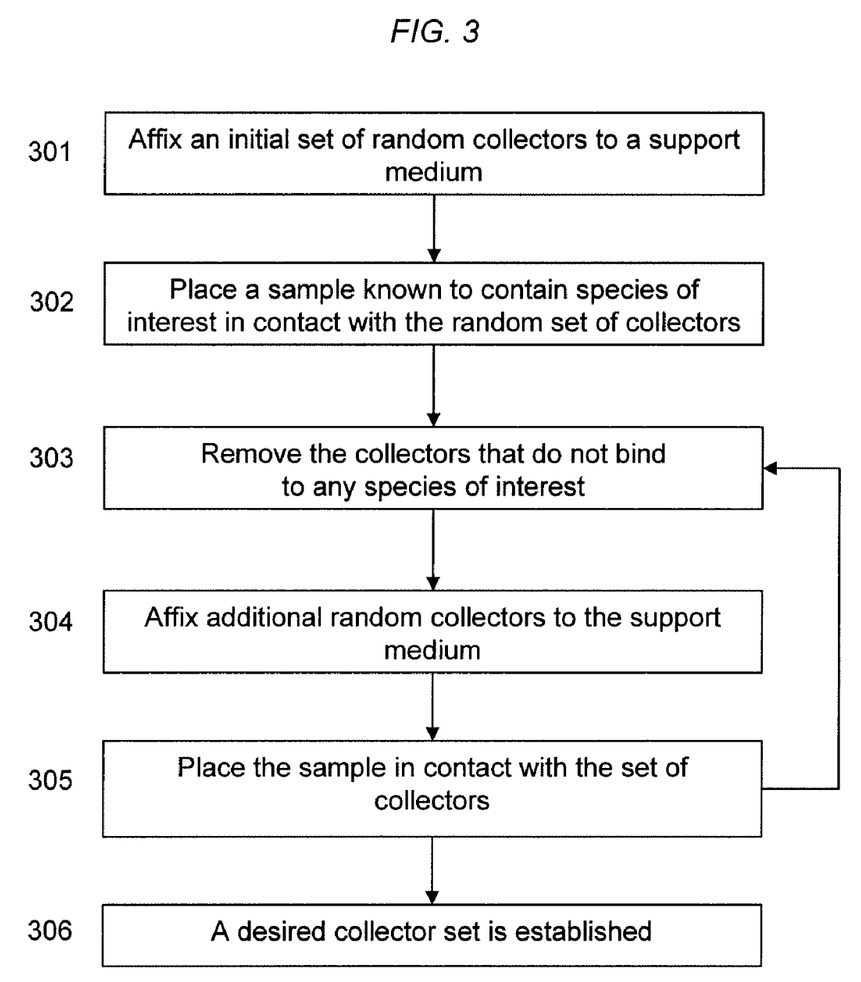
FIG. 3 illustrates a flow diagram in accordance with an embodiment of the present invention.

In one embodiment, a suitable set of nucleic acid molecules is developed, for example, as depicted in FIG. 3. An initial a random set of nucleic acid molecules (collectors) is established and affixed to a support medium 301; the set is exposed to a sample known to contain species of interest 302 and at least a portion of the random set of nucleic acid molecules will bind to the species of interest; nucleic acid molecules that do not bind to the species are removed 303; the remaining slots within the library are again filled with random nucleic acid molecules 304; the sample is placed in contact with the nucleic acid molecules 305; and the process is repeated until a suitable set of nucleic acid molecules is developed 306. FIG. 2 also depicts a method of creating such suitable set of collectors. The ability of the library to extract concentration information from the blood serum is thereby amplified with each iteration.

In another embodiment, the collector set may be fragments of genomic DNA. One skilled in the art will readily appreciate means by which genomic DNA may be fragmented. One method of creating fragments of genomic DNA is by the use of restriction enzymes (also known as restriction endonucleases). A restriction enzyme will recognize specific base sequences of DNA and cut the DNA at that site. The restriction enzyme's cut may produce "blunt" ends (i.e., strand incisions immediately opposite to the other) or "sticky" ends (i.e., staggered incisions in which one end protrudes). Common restriction enzymes include, but are not limited to EcoRI, BamHI, HindIII, MstII, TaqI, NotI, HindfI and AuII. Additional types of restriction enzymes may be used with various embodiments of the present invention.

In another embodiment, the collector set may comprise different antibodies, each of which is capable of binding specifically to a proteins, protein fragment and/or peptide. The antibodies may be monoclonal or polyclonal. One of skill in the art will be able to produce the antibodies described herein without undue experimentation.

Methods of preparing monoclonal antibodies are known in the art. For example, monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a protein of interest or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) *Monoclonal Antibodies: Principles and Practice* Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

The present invention is also directed to a kit for positive selection of species of interest from a sample. The kit is useful for practicing the inventive method of positive selection of species of interest from sample including the extraction of a composition comprising a plurality of species of interest and a lower concentration of a high abundance species of interest. In one embodiment the selected species of interest may be used in proteomic analysis.

Additionally, the invention is directed to a kit for obtaining a blood chemistry signature. The kit is useful for practicing the inventive method of positive selection of species of interest from a blood sample and generating a blood chemistry signature; for example, by performing mass spectrometric analysis of the species of interest.

The kit is an assemblage of materials or components, including at least one set of collectors. Thus, in some embodiments the kit contains a set of collectors to selectively bind species of interest from a sample.

The exact nature of the components configured in the inventive kit depends on its intended purpose. For example, some embodiments of the kit are configured for the purpose of positive selection of proteins and/or peptides from a sample. Other embodiments of the kit are configured for analyzing selected proteins and/or peptides by obtaining a blood chemistry signature.

In one embodiment, the kit is configured particularly for the purpose of selecting proteins and/or peptides of interest from a sample obtained from mammalian subjects. In an alternative embodiment the kit is configured particularly for the purpose of selecting proteins and/or peptides of interest from a sample obtained from human subjects. In other embodiments, the kit may be configured for positive selection of proteins and/or peptides from a subject's bodily fluids. In particular embodiments, the kits are configured for positive selection of proteins and/or peptides from whole blood, blood serum and/or blood plasma.

Instructions for use may be included in the kit. "Instructions for use" typically include a tangible expression describing the technique to be employed in using the components of the kit to effect a desired outcome, such as to select proteins of interest from a sample or to obtain a blood chemistry signature. Instruction for use may include instructions to practice the inventive methods as described herein. Optionally, the kit also contains other useful components, such as, Petri dishes, columns, media for which the collectors may be affixed (e.g., glass beads, agarose beads, cellulose beads, plastic chips, silicone chips, glass chips), fluorescent labels, fluorophores, chromophores, isotopic labels, quantum dots, filtrate tubes, filter media, sample reservoir, filtrate receiver, diluents, buffers, eluates, syringes, applicators, pipetting or measuring tools, test tubes, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in species selection kits. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing collectors (e.g., DNA, RNA, aptamers, antibodies). The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Genomic DNA is digested by one or more restriction enzymes. The collectors are digested fragments of the genomic DNA. The fragments of genomic DNA are affixed to support media. One skilled in the art will appreciate that nucleic acids can be affixed, attached or immobilized to support media in a variety of ways. "Immobilized" as used herein refers to the association or binding between the nucleic acid sequences and the support medium that is sufficient to be stable under the conditions of binding, washing, analysis, and as necessitated by various embodiments of the present invention. The binding may be covalent or non-covalent. "Non-covalent" as used herein refers to one or more electrostatic, hydrophilic, or hydrophobic interactions. Further, "non-covalent" binding may also refer to the covalent attachment of a molecule, such as, streptavidin to the support medium and the non-covalent binding of the nucleic acids to the streptavidin. "Covalent binding" as used herein refers to two moieties, the support medium and the nucleic acid sequence, that are attached by at least one bond. Covalent bonds may be formed directly between the nucleic acid sequence and the support medium or may be formed by a cross linker or by inclusion of a specific reactive group on either the support medium or the nucleic acid sequence or both. Immobilization may include a combination of covalent and non-covalent interactions.

The support media (with the affixed fragments of genomic DNA) are placed in a column. A sample containing proteins and/or peptides of interest is allowed to flow through the column and thus contact the collectors. As the sample flows through the collectors, the proteins and/or peptides of interest bind to the fragments of DNA. Optionally, a buffer is used to unbind the peptides and/or proteins of interest from the collectors. The sample containing the peptides and/or proteins of interest is placed in a mass spectrometer. If the sample is whole blood, blood serum or blood plasma, the mass spectrum obtained depicts a blood chemistry signature. The blood chemistry signature is used for proteomic analysis. Much information may be obtained from proteomic analysis; for example, proteomic analysis may yield better understanding of metabolic pathways, or assist in predicting the clinical outcome of therapeutic interventions to a disease. The presence of a disease may also be detected from the proteomic analysis. A subject's physiological state may also be determined from the proteomic analysis; for example hunger, pain, reaction to a drug.

In another option, a buffer is used to unbind the DNA fragments from the glass beads. The sample containing the peptides and/or proteins of interest bound to the fragments of DNA is placed in a mass spectrometer. If the sample is whole blood, blood serum or blood plasma, the mass spectrum obtained depicts a blood chemistry signature. The blood chemistry signature may also be used for proteomic analysis as described above.

Example 2

Figure 1A:
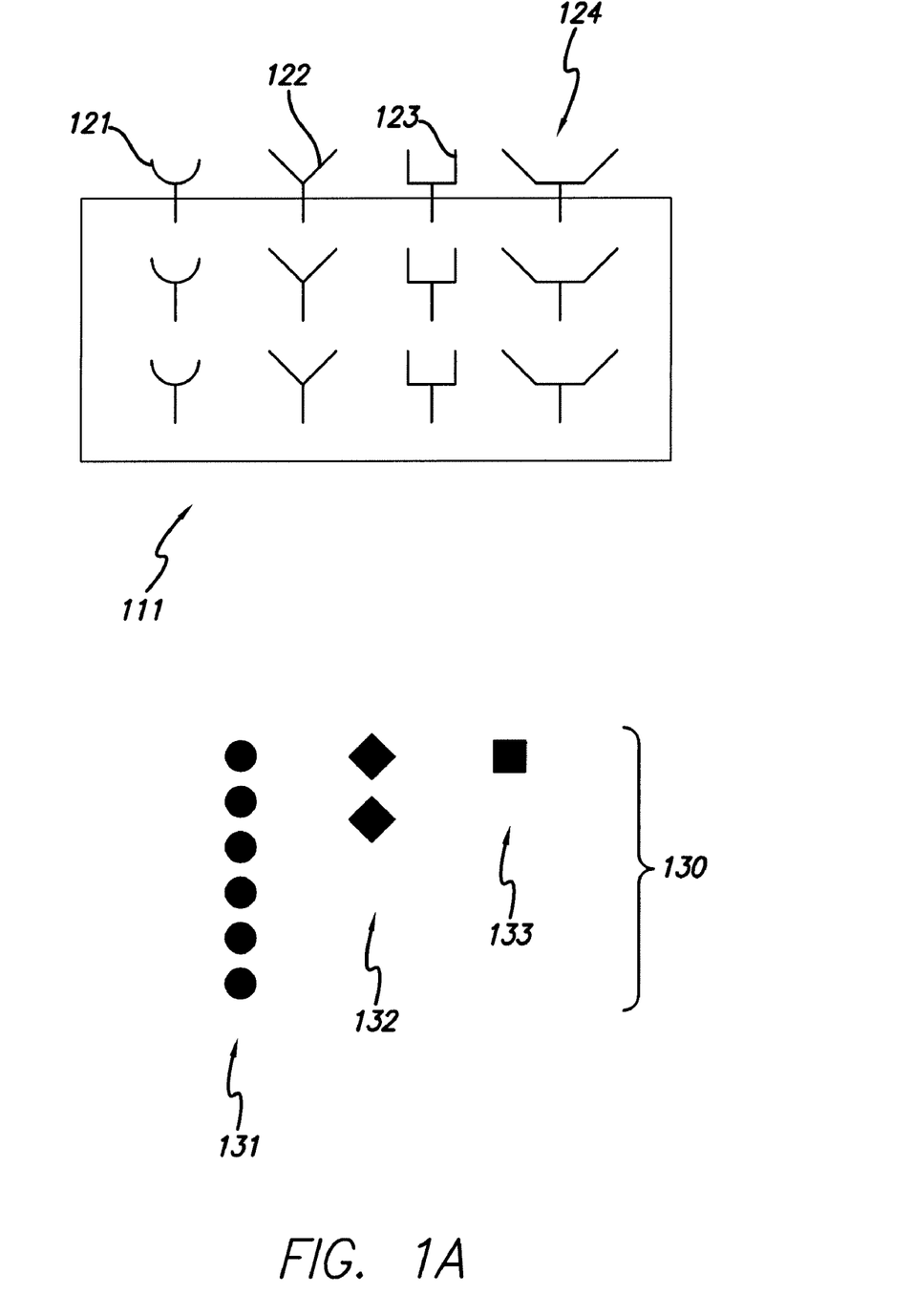
FIG. 1 illustrates an embodiment of the present inventive method of positive selection of species of interest.

With reference to FIG. 1, the collectors 121, 122, 123, 124 are affixed to the support media 111 and a sample 130 containing species of interest is provided. The sample 130 is placed in contact with the collectors 121, 122, 123, 124 (B). Selection of species of interest 131, representing a high abundance species, is limited because the collector set has a limited number of collectors that bind to species of interest 131. Thus, the influence that the high abundance species 131 may have on a mass spectra is "clipped," i.e., limited such to allow better detection of low abundance species.

Partially filled collectors 122 and 123 indicate that species 132 and 133 are present at an intermediate concentration. The proportional binding of the species 132 and 133 to collectors 122 and 123 can be mapped to the particular concentration of species 132 and 133 in the sample. Completely empty collector 124 indicates that the species is not present in the sample at detectable levels.

Figure 1B:
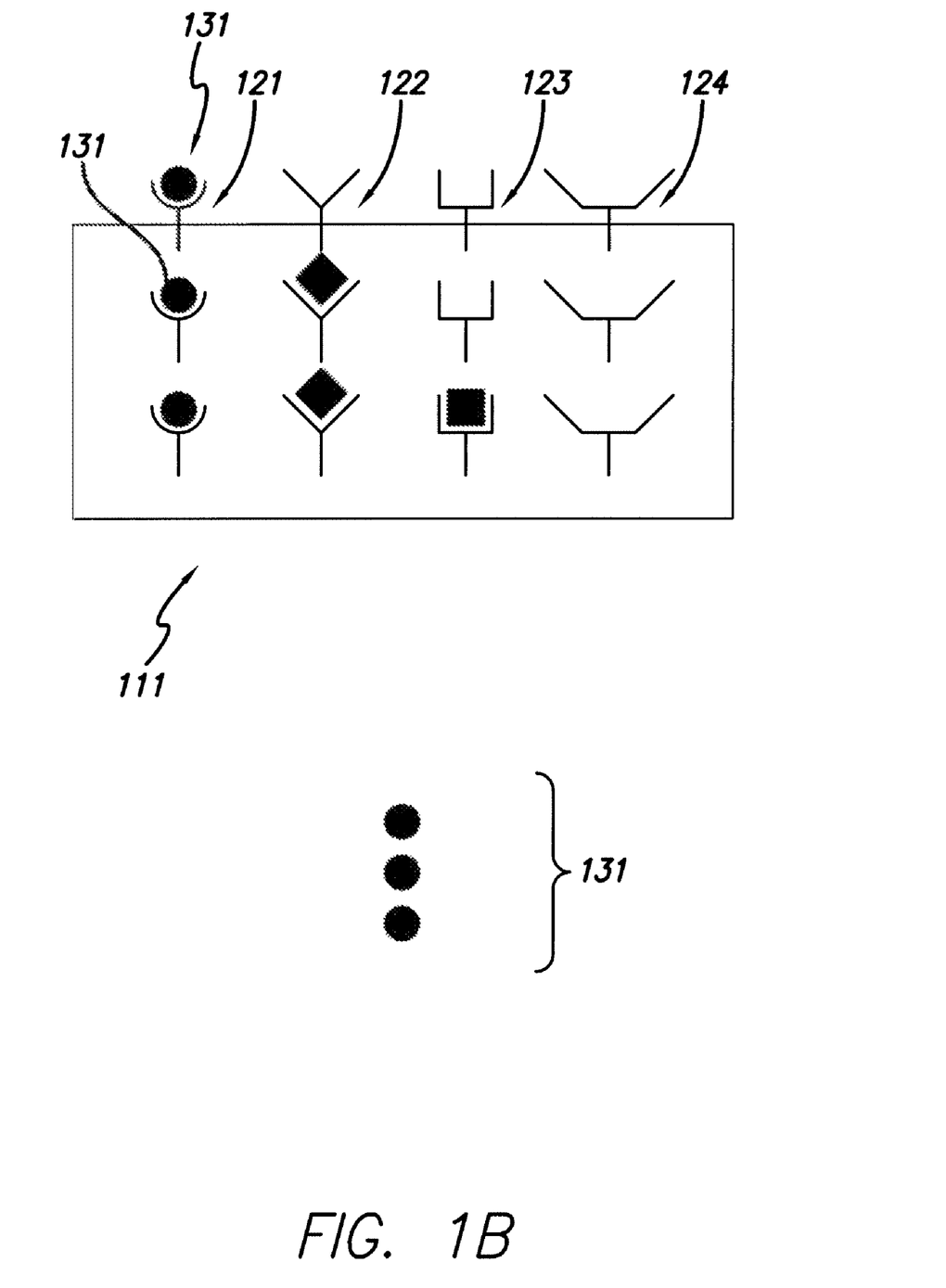
Figure 2A:
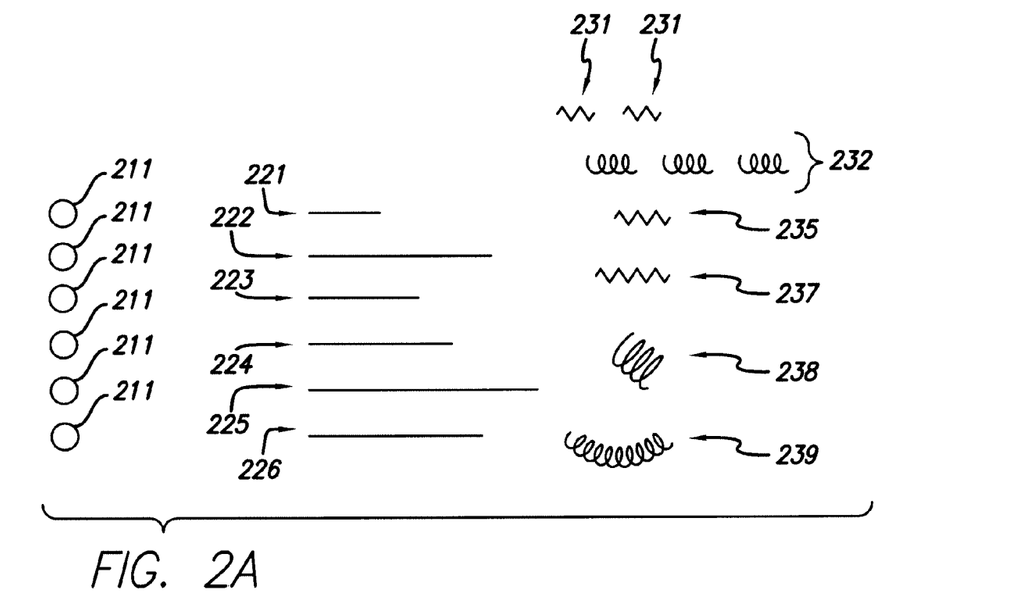
FIG. 2 illustrates an embodiment of the present invention where a collector set is created using nucleic acid molecules.
Figure 2B:
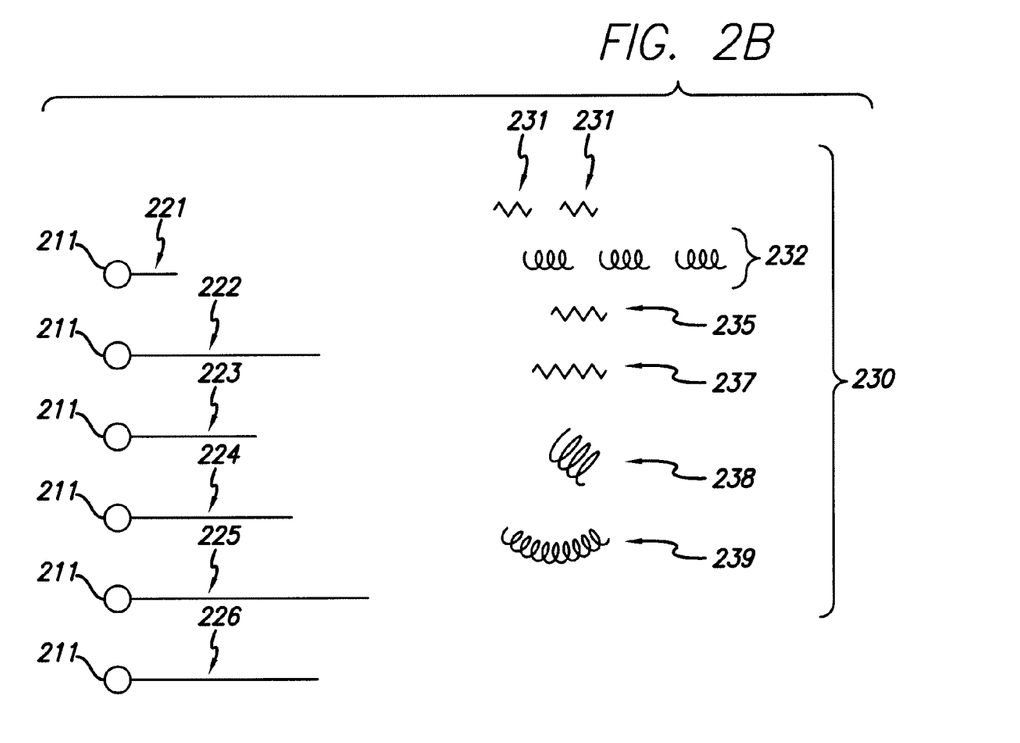
Figure 2C:
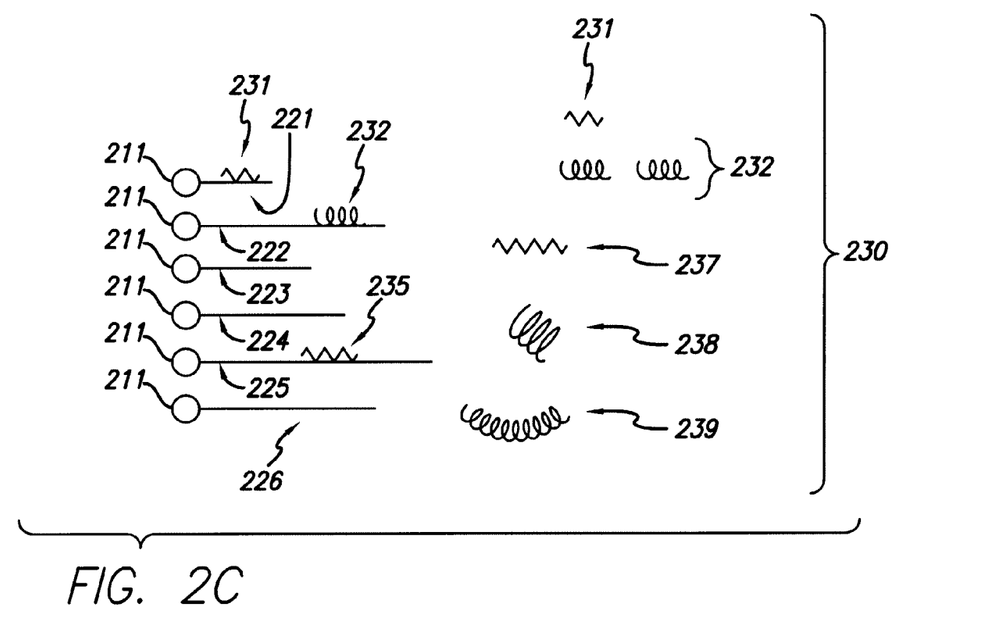
Figure 2D:
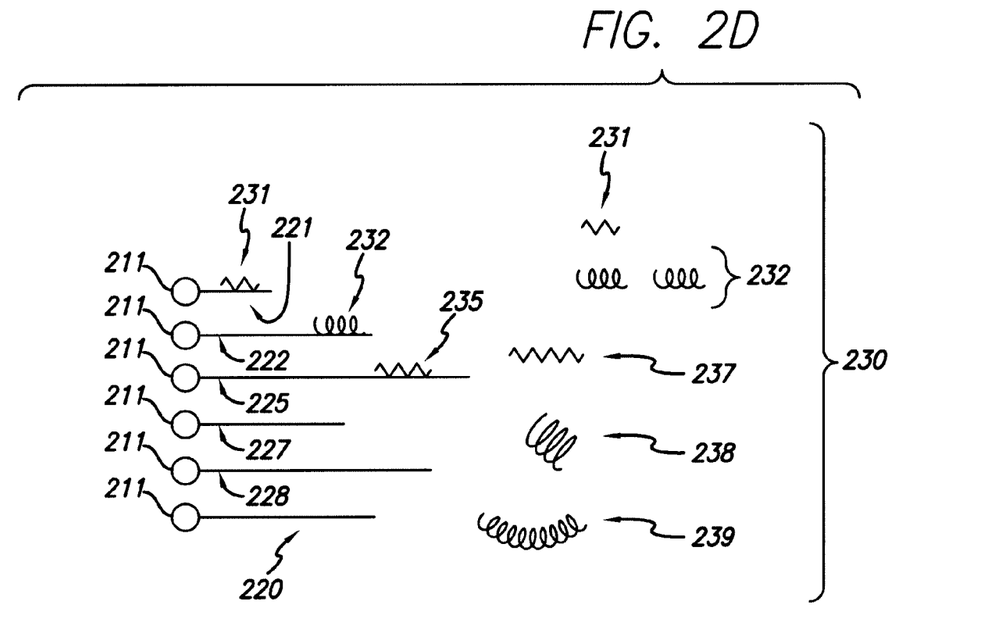
Figure 2E:
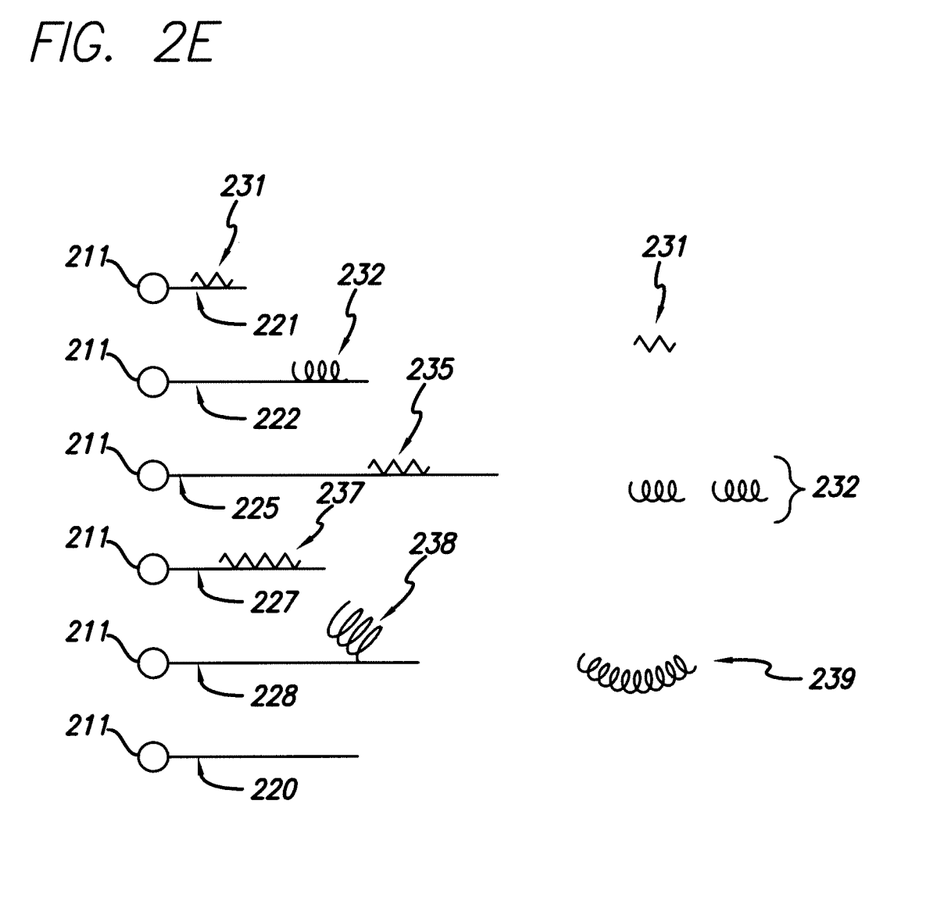

While FIG. 1B depicts three species of interest 131 are left behind, it not intended that the high abundance species 131 is only reduced by a half. As indicated herein, high abundance species are frequently of 11 orders of magnitude higher than low abundance species of interest. Thus, in a typical sample, there may be a higher quantity of the high abundance species 131 left behind in the sample after the desired species of interest are extracted.

After the sample is placed in contact with the collectors, the collectors may be separated from the support media. The separated collectors (and the bound species of interest) may be placed in a mass spectrometer for analysis. Alternatively, rather than separating the collectors from the support medium, the species of interest may be separated from the collectors. In this embodiment, the species of interest are placed in a mass spectrometer for analysis.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method to extract a composition comprising a plurality of species of interest and a lower concentration of a high abundance species of interest from a sample, comprising:
    providing a plurality of collectors capable of binding specifically with a sufficient binding affinity to a plurality of species of interest in a sample comprising at least one high abundance species of interest, wherein the quantity of a collector specific for the at least one high abundance species of interest is at least 50% less than the quantity of the at least one high abundance species of interest in the sample;
    placing the sample in contact with the plurality of collectors, whereby at least a portion of the plurality of collectors binds to the species of interest to generate bound species of interest, and at least 75% of the collector specific for the at least one high abundance species of interest binds to the at least one high abundance species of interest to generate bound high abundance species of interest; and
    separating the bound species of interest and the bound high abundance species of interest from the sample to generate an extracted composition, whereby the concentration of the at least one high abundance species of interest in the extracted composition is lower than the concentration of the at least one high abundance species of interest in the sample,
    wherein the species of interest is selected from the group consisting of a protein, protein fragment, peptide and combinations thereof, and the plurality of collectors comprise a collector type selected from the group consisting of a nucleic acid molecule, amino acid, peptide, protein, aptamer, antibody, plasmid, phage, cofactor, metal ion and combinations thereof.

2. The method of claim 1, wherein the at least one high abundance species of interest is selected from the group consisting of albumin, immunoglobulin, transferrin and combinations thereof.

3. The method of claim 1, wherein the quantity of the collector specific for the at least one high abundance species of interest is at least 75% less than the quantity of the at least one high abundance species of interest in the sample.

4. The method of claim 1, wherein the quantity of the collector specific for the at least one high abundance species of interest is at least 85% less than the quantity of the at least one high abundance species of interest in the sample.

5. The method of claim 1, wherein the quantity of the collector specific for the at least one high abundance species of interest is at least 95% less than the quantity of the at least one high abundance species of interest in the sample.

6. The method of claim 1, wherein placing the sample in contact with the plurality of collectors binds at least 85%, 90%, 95%, or 99% of the collector specific for the at least one high abundance species of interest to the at least one high abundance species of interest to generate the bound high abundance species of interest.

7. The method of claim 1, wherein separating the bound species of interest and the bound high abundance species of interest from the sample comprises:
    separating collectors bound to the species of interest and collectors bound to the high abundance species of interest from the sample; and/or
    separating the bound species of interest and the bound high abundance species of interest from the collectors.

8. The method of claim 1, wherein the sample is selected from the group consisting of body fluids, whole blood, plasma, serum, cerebral spinal fluid (CSF), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysate, tumor tissue, hair, skin, buccal scraping, nail, bone marrow, cartilage, prion, bone powder, ear wax, tumor samples and combinations thereof.

9. The method of claim 8, wherein the sample is whole blood, blood plasma or blood serum.

10. The method of claim 1, wherein the nucleic acid molecule is a DNA aptamer or a RNA aptamer.

11. The method of claim 1, wherein the collector type comprises genomic DNA cleaved into segments.

12. The method of claim 1, wherein the collector type is an antibody capable of binding specifically to a particular protein, protein fragment, and/or peptide.

13. A method for producing a set of collectors to extract a composition comprising a plurality of species of interest and a lower concentration of a high abundance species of interest from a sample, comprising:
    providing a set of random collectors;
    exposing a sample comprising a plurality of species of interest to the set of random collectors;
    removing at least one unbound collector;
    providing at least one additional random collector; and
    repeating the process until a desired collector set is obtained.

14. The method of claim 13, wherein the collectors comprise a collector type that is a nucleic acid molecule.

15. The method of claim 14, wherein the nucleic acid molecule is a DNA aptamer or a RNA aptamer.

16. The method of claim 13, wherein the species of interest is selected from the group consisting of a protein, protein fragment, peptide and combinations thereof.

17. A kit for extracting a composition comprising a plurality of species of interest and a lower concentration of a high abundance species of interest from a sample, comprising:
    a plurality of collectors capable of binding specifically with a sufficient binding affinity to a plurality of species of interest in a sample comprising at least one high abundance species of interest, wherein the quantity of a collector specific for the at least one high abundance species of interest is at least 50% less than the quantity of the at least one high abundance species of interest in the sample; and
    instructions for using the plurality of collectors to extract a composition comprising the plurality of species of interest and a lower concentration of the high abundance species of interest from the sample,
    wherein the species of interest is selected from the group consisting of a protein, protein fragment, peptide and combinations thereof, and the plurality of collectors comprise a collector type selected from the group consisting of a nucleic acid molecule, amino acid, peptide, protein, aptamer, antibody, plasmid, phage, cofactor, metal ion and combinations thereof.

18. The kit of claim 17, wherein the nucleic acid molecule is a DNA aptamer or RNA aptamer.

19. The kit of claim 17, wherein the collector type comprises genomic DNA.

20. The kit of claim 17, wherein the collector type is an antibody capable of binding specifically to a particular protein, protein fragment, or peptide.

21. A method of obtaining a blood chemistry signature, comprising:
    obtaining a sample from a subject, wherein the sample comprises at least one high abundance species of interest;
    providing a plurality of collectors capable of binding specifically with a sufficient binding affinity to a plurality of species of interest in the sample, wherein the quantity of a collector specific for the at least one high abundance species of interest is at least 50% less than the quantity of the at least one high abundance species of interest in the sample;
    placing the sample in contact with the plurality of collectors, whereby at least a portion of the plurality of collectors binds to the species of interest to generate bound species of interest, and at least 75% of the collector specific for the at least one high abundance species of interest binds to the at least one high abundance species of interest to generate bound high abundance species of interest;
    separating the bound species of interest and the bound high abundance species of interest from the sample to generate an extracted composition, whereby the concentration of the at least one high abundance species of interest in the extracted composition is lower than the concentration of the at least one high abundance species of interest in the sample; and
    performing a mass spectrometric analysis of the extracted composition,
    wherein the species of interest is selected from the group consisting of a protein, protein fragment, peptide and combinations thereof, and the plurality of collectors comprise a collector type selected from the group consisting of a nucleic acid molecule, amino acid, peptide, protein, aptamer, antibody, plasmid, phage, cofactor, metal ion and combinations thereof.

22. The method of claim 21, wherein the at least one high abundance species of interest is selected from the group consisting of albumin, immunoglobulin, transferrin and combinations thereof.

23. The method of claim 21, wherein the quantity of the collector specific for the at least one high abundance species of interest is at least 75% less than the quantity of the at least one high abundance species of interest in the sample.

24. The method of claim 21, wherein the quantity of the collector specific for the at least one high abundance species of interest is at least 85% less than the quantity of the at least one high abundance species of interest in the sample.

25. The method of claim 21, wherein the quantity of the collector specific for the at least one high abundance species of interest is at least 95% less than the quantity of the at least one high abundance species of interest in the sample.

26. The method of claim 21, wherein placing the sample in contact with the plurality of collectors binds at least 85%, 90%, 95%, or 99% of the collector specific for the at least one high abundance species of interest to the at least one high abundance species of interest to generate the bound high abundance species of interest.

27. The method of claim 21, wherein separating the bound species of interest and the bound high abundance species of interest from the sample comprises:
    separating collectors bound to the species of interest and collectors bound to the high abundance species of interest from the sample; and/or
    separating the bound species of interest and the bound high abundance species of interest from the collectors.

28. The method of claim 21, wherein the sample is selected from the group consisting of body fluids, whole blood, plasma, serum, cerebral spinal fluid (CSF), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysate, tumor tissue, hair, skin, buccal scraping, nail, bone marrow, cartilage, prion, bone powder, ear wax, tumor samples and combinations thereof.

29. The method of claim 28, wherein the sample is whole blood, blood plasma or blood serum.

30. The method of claim 21, wherein the nucleic acid molecule is a DNA aptamer or a RNA aptamer.

31. The method of claim 21, wherein the collector type comprises genomic DNA cleaved into segments.

32. The method of claim 21, wherein the collector type is an antibody capable of binding specifically to a particular protein, protein fragment, and/or peptide.

33. A kit for obtaining a blood chemistry signature, comprising:
    a plurality of collectors capable of binding specifically with a sufficient binding affinity to a plurality of species of interest in a sample comprising at least one high abundance species of interest, wherein the quantity of a collector specific for the at least one high abundance species of interest is at least 50% less than the quantity of the at least one high abundance species of interest in the sample;
    instructions for using the plurality of collectors to extract a composition comprising a plurality of species of interest and a lower concentration of a high abundance species of interest from a sample; and
    instructions for analyzing the extracted composition,
    wherein the species of interest is selected from the group consisting of a protein, protein fragment, peptide and combinations thereof, and the plurality of collectors comprise a collector type selected from the group consisting of a nucleic acid molecule, amino acid, peptide, protein, antibody, plasmid, phage, cofactor, metal ion and combinations thereof.

34. The kit of claim 33, wherein the nucleic acid molecule is a DNA aptamer or a RNA aptamer.

35. The kit of claim 33, wherein the collector type comprises genomic DNA cleaved into segments.

36. The kit of claim 33, wherein the collector type is an antibody capable of binding specifically to a particular protein, protein fragment, and/or peptide.

* * * * *